United States Patent [19]
Durant et al.

[11] 4,375,472
[45] Mar. 1, 1983

[54] AMIDINOSULPHONIC ACID DERIVATIVES

[75] Inventors: Graham J. Durant, Welwyn Garden City; Rodney C. Young, Bengeo, both of England; Zev Tashma, Jerusalem, Israel

[73] Assignee: Smith Kline & French Laboratories Limited, Welwyn Garden City, England

[21] Appl. No.: 209,449

[22] Filed: Nov. 24, 1980

Related U.S. Application Data

[62] Division of Ser. No. 90,949, Nov. 5, 1979, Pat. No. 4,265,896, which is a division of Ser. No. 940,063, Sep. 6, 1978, Pat. No. 4,210,658.

[30] Foreign Application Priority Data

Sep. 8, 1977 [GB] United Kingdom ............... 37468/77

[51] Int. Cl.³ .................. A61K 31/42; A61K 31/425; C07D 249/08; C07D 285/12
[52] U.S. Cl. .................................. 424/269; 424/270; 424/272; 548/127; 548/128; 548/129; 548/134; 548/134; 548/135; 548/136; 548/138; 548/186; 548/193; 548/205; 548/213; 548/214; 548/225; 548/228; 548/229; 548/232; 548/233; 548/235; 548/243; 548/245; 548/247; 548/255; 548/265; 548/266; 548/269
[58] Field of Search ............... 548/205, 193, 186, 214, 548/213, 225, 138, 228, 229, 232, 233, 235, 202, 255, 266, 247, 265, 267, 269, 247, 243, 127, 128, 129, 134, 135, 136; 424/269, 270, 272

[56] References Cited

U.S. PATENT DOCUMENTS

| | | | |
|---|---|---|---|
| 3,734,924 | 5/1973 | Black et al. | 548/342 |
| 3,736,331 | 5/1973 | Black et al. | 546/331 |
| 4,090,026 | 5/1978 | Durant et al. | 546/331 |
| 4,109,003 | 8/1978 | Durant et al. | 424/273 R |
| 4,118,502 | 10/1978 | Durant et al. | 546/331 |
| 4,154,838 | 5/1979 | Durant et al. | 546/331 |
| 4,210,658 | 7/1980 | Durant et al. | 424/273 R |

OTHER PUBLICATIONS

*Official Gazette*, Aug. 19, 1980, pp. 1027, 1036 and 1058.

*Primary Examiner*—Alton D. Rollins
*Attorney, Agent, or Firm*—Joan S. Keps; Richard D. Foggio; Alan D. Lourie

[57] ABSTRACT

Amidinosulphonic acid derivatives carrying an unsaturated nitrogen heterocycle-containing substituent, representative of which are N-methyl-N'[2-(5-methyl-4-imidazolylmethylthio)- ethyl] amidinosulphonic acid and N-methyl-N'-[2-(3-chloropyrid-2-ylmethylthio) ethyl] amidinosulphonic acid, are histamine $H_2$-receptor antagonists.

3 Claims, No Drawings

AMIDINOSULPHONIC ACID DERIVATIVES

This is a division of application Ser. No. 90,949 filed Nov. 5, 1979, now U.S. Pat. No. 4,265,896, which is a division of application Ser. No. 940,063 filed Sept. 6, 1978, now U.S. Pat. No. 4,210,658.

This invention relates to amidinosulphonic derivatives, processes for the preparation of such derivatives and pharmaceutical compositions containing the derivatives.

Many physiologically-active substances elicit their biological actions by interaction with specific sites known as receptors. Histamine is such a substance and has a number of biological actions. Those biological actions of histamine which are inhibited by drugs commonly called "antihistamines", of which mepyramine, diphenhydramine and chlorpheniramine are typical examples, are mediated through histamine $H_1$-receptors. However, others of the biological actions of histamine are not inhibited by "antihistamines" and actions of this type which are inhibited by burimamide are mediated through receptors which are termed histamine $H_2$-receptors, and which may be defined as those histamine receptors which are not blocked by mepyramine but are blocked by burimamide. Compounds which block histamine $H_2$-receptors are referred to as histamine $H_2$-receptor antagonists.

Blockade of histamine $H_2$-receptor antagonists is of utility in inhibiting the biological actions of histamine which are not inhibited by "antihistamines". Histamine $H_2$-receptor antagonists are therefore useful, for example, as inhibitors of gastric acid secretion, as anti-inflammatory agents and as agents which act on the cardiovascular system, for example as inhibitors of the effects of histamine on blood pressure.

According to the present invention there are provided compounds of the formula

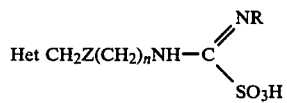

where Het is a nitrogen-containing 5 or 6 membered heterocyclic group, for example in imidazolyl, pyridyl, thiazolyl, isothiazolyl, oxazolyl, isoxazolyl, triazolyl or thiadiazolyl group optionally substituted by a lower alkyl, hydroxyl, lower alkoxy, halogen, trifluoromethyl, hydroxymethyl or amino group; Z is sulphur or a methylene group; n is 2 or 3; and R is hydrogen, lower alkyl or Het $CH_2Z(CH_2)_n$.

The compounds of formula I show activity as histamine $H_2$-receptor antagonists.

It will be understood that the structure illustrated in formula I is only one of several representations and that other tautomeric forms are covered by the present invention. The present invention also includes pharmaceutically acceptable salts of the compounds of formula I. The salts can be acid addition salts with inorganic acids, for example hydrochloric, hydrobromic, hydroiodic or sulphuric acids, or with organic acids for example maleic acid. The salts can alternatively be with metals or bases, e.g. alkali metal salts such as sodium salts.

Throughout the present specification and claims the term 'lower alkyl' means an alkyl group containing from 1 to 4 carbon atoms. In a preferred group of compounds, Z is sulphur, and n is 2. It is also preferred that Het should be an imidazolyl group optionally substituted by methyl or halogen; a thiazolyl group; an isothiazolyl group or a pyridyl group optionally substituted by methyl, hydroxyl or halogen.

Preferred compounds of formula I by virtue of their particularly interesting activity as histamine $H_2$-receptor antagonists are:

N-methyl-N'-[2-(4-methyl-5-imidazolyl methylthio)ethyl]-amidinosulphonic acid and N-methyl-N'-[2-(3-chloropyrid-2-ylmethylthio)ethyl]amidinosulphonic acid.

The compounds of formula I can be produced by reacting a compound of formula

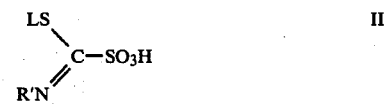

(where L is lower alkyl, for example methyl, and R' is lower alkyl or Het $CH_2Z(CH_2)_n$) with a compound of formula $R^2NH_2$ (were $R^2$ is Het $CH_2Z(CH_2)_n$ or if R' is Het $CH_2Z(CH_2)_n$, hydrogen or lower alkyl). Salts of the compounds of formula I which are produced can be prepared by known methods.

The compounds of formula II can be produced by known methods. When Z is a methylene group, the compounds of formula I can also be prepared by reacting one or other of the corresponding compounds of formula

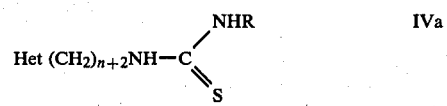

or

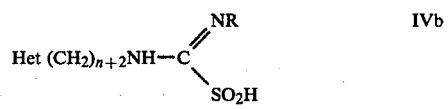

(where Het and R have the above significance, and n is as hereinbefore defined) with an oxidising agent, for example peracetic acid.

The compounds of this invention block histamine $H_2$-receptors: that is, they inhibit the biological actions of histamine which are not inhibited by antihistamines such as mepyramine but are inhibited by burimamide. For example, they inhibit histamine-stimulated secretion of gastric acid from the lumen-perfused stomachs of rats anaesthetised with urethane, at doses of from 0.5 to 256 micromoles per kilogram intravenously. Their activities as histamine $H_2$-antagonists are also demonstrated by their ability to inhibit other actions of histamine which are not mediated through histamine $H_1$-receptors. For example, they inhibit the actions of histamine on the isolated guinea pig atrium and isolated rat uterus. They inhibit the basal secretion of gastric acid and also gastric acid secretion stimulated by pentagastrin or by food. They have also been found to inhibit the vasodilator action of histamine when blood pressure measurements in the anaesthetised cat, using doses of from 0.5 to 256 micromoles per kilogram intravenously, were carried out. The potency of the compounds is illustrated by an effective dose producing 50% inhibition of gastric acid secretion in the anaesthetised rat and producing 50% inhibition of histamine-induced tachycardia in the isolated guinea pig atrium (less than $10^{-4}$ Molar).

The invention further provides pharmaceutical compositions comprising a compound of formula I in its neutral form or in the form of a pharmaceutically acceptable salt with an acid or base, and a pharmaceutical carrier.

The pharmaceutical carrier can be solid or liquid. Examples of solid carriers are lactose, terra alba, sucrose, talc, gelatin, agar, pectin, acacia, magnesium stearate and stearic acid. Examples of liquid carriers are syrup, peanut oil, olive oil and water.

If a solid carrier is used, the compositions can be prepared in the form of a tablet, capsule, troche or lozenge. The amount of solid carrier in a unit dosage form is generally from about 25 mg to about 300 mg. If a liquid carrier is used, the composition can be in the-form of a syrup, emulsion, soft gelatin capsule, a sterile injectable liquid contained for example in an ampoule, or an aqueous or non-aqueous liquid suspension. The pharmaceutical compositions can be prepared by conventional techniques involving procedures such as mixing, granulating and compressing or dissolving the ingredients as appropriate to the desired form of composition. Compositions of the invention are preferably in dosage unit form. The amount of active ingredient in each dosage unit will in general be an effective amount to block histamine $H_2$-receptors in the subject being treated. Each dosage unit preferably contains the active ingredient in an amount of from about 50 mg to about 250 mg.

The active ingredient will preferably be administered one to six times per day. The daily dosage regimen will generally be from about 150 mg to about 1500 mg. The route of administration can be oral or parenteral.

The invention also provides a method of blocking histamine $H_2$-receptors which comprises administering to an animal a compound of formula I or a pharmaceutically acceptable salt thereof.

In the treatment of certain conditions, for example inflammation, and in inhibiting the actions of histamine on blood pressure, a combination of the histamine $H_2$-antagonists of the invention with histamine $H_1$-antagonists is useful.

The invention is illustrated by the following Examples in which all temperatures are in degrees centigrade.

EXAMPLE 1

N-Methyl-N'-[2-(5-methyl-4-imidazolylmethylthio)ethyl]-amidinosulphonic acid

A solution of 1.43 g (0.0085 mole) of 2-(5-methyl-4-imidazolylmethylthio)ethylamine in dry acetonitrile (150 ml) was added dropwise, with stirring, to a solution of 1.43 g (0.0084 mole) of 1-methylthio-1-methyliminomethanesulphonate in dry acetonitrile (150) at 50°, giving an immediate white precipitation. After further warming at 70° for one hour, the mixture was stripped to dryness, dissolved in methanol and absorbed onto silica gel. Chromatography on a column of silica gel was performed with ethylacetate/methanol (20:1), and the crude product recrystallised from isopropanol to give the title compound, 0.46 g.m.p. 162.5°–163.5° as an almost colourless crystalline solid.

(Found: C, 36.8; H, 5.6; N, 19.1; S, 21.7%. $C_9H_{16}N_4O_3S_2$ requires: C, 37.0; H, 5.5; N, 19.2; S, 21.9%.)

EXAMPLE 2

N-Methyl-N'-[2-(3-chloropyrid-2-ylmethylthio)ethyl]-amidinosulphonic acid

A solution of 2-(3-chloropyrid-2-ylmethylthio)ethylamine (2.03 g) in dry acetonitrile (150 ml) was added dropwise, with stirring, to a solution of 1-methylthio-1-methyliminomethanesulphonate (1.69 g) in dry acetonitrile (150 ml) at 50°. The mixture was stirred at 60° for 30 minutes and then allowed to cool. The mixture was stripped to dryness, dissolved in methanol and absorbed onto silica gel. Chromatography on a column of silica gel produced a viscous oil which was collected by eluting the column with a chloroform/methanol mixture and evaporating off the solvent. The viscous oil analysed by micro-analysis and nuclear magnetic resonance spectroscopy to the title compound.

pyridyl-6-$\underline{H}$, doublet of doublets at $\delta 8.48$, integral 1.0 protons.

pyridyl-4-$\underline{H}$, doublet of doublets at $\delta 7.92$, integral 1.0 protons.

pyridyl-3-$\underline{H}$, doublet of doublets at $\delta 7.37$, integral 1.0 protons.

pyridyl-$\underline{CH_2}$-S, singlet at $\delta 4.00$, integral 2.0 protons.

>N-$\underline{CH_2}$-CH$_2$S, multiplet at $\delta 3.72$, obscured by solvent resonance.

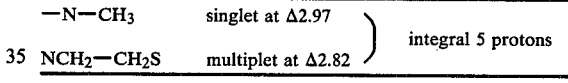

(Found: C, 36.30; H, 4.29; N, 12.96; S, 19.86%. $C_{10}H_{14}ClN_3O_3S_2$ requires: C, 37.09; H, 4.36; N, 12.98; S, 19.80%.)

EXAMPLE 3

N,N'-bis-[2-(3-chloropyrid-2-ylmethylthio)ethyl]amidinosulphonic acid

A solution of 2-(3-chloropyrid-2 ylmethylthio)ethylamine (4.06 g) in dry acetonitrile (200 ml) was added dropwise, with stirring, to a solution of 1-methylthio-1-methyliminomethanesulphonate (1.69 g) in dry acetonitrile (150 ml) at 50°. The mixture was stired at 60° for 1 hour and then allowed to cool. The mixture was evaporated to dryness, dissolved in methanol and absorbed onto silica gel. Chromatography on a column of silica gel produced a viscous oil which was collected by eluting the column with a chloroform/methanol mixture and evaporating off the solvent. The viscous oil analysed by microanalysis and nuclear magnetic resonance spectroscopy to the title compound.

pyridyl-6-$\underline{H}$, doublet of doublets at $\delta 8.45$, integral 1.0 protons.

pyridyl-4-$\underline{H}$, doublet of doublets at $\delta 7.89$, integral 1.0 protons.

pyridyl-3-$\underline{H}$, doublet of doublets at $\delta 7.34$, integral 1.0 protons.

pyridyl-$\underline{CH_2}$-S, singlet at $\delta 3.97$, integral 2.0 protons.

N-$\underline{CH_2}$-CH$_2$S, multiplet at $\delta 3.6$, obscured by solvent resonance.

N-CH$_2$-$\underline{CH_2}$S, multiplet at $\delta 2.73$, integral 2.0 protons.

EXAMPLE 4

Substitution of the following amines
(a) 2-(5-ethyl-4-imidazolylmethylthio)ethylamine
(b) 2-(5-bromo-4-imidazolylmethylthio)ethyalmine
(c) 2-(5-trifluoromethyl-4-imidazolyl)methylthio)ethylamine
(d) 2-(5-hydroxymethyl-4-imidazolyl)methylthio)ethylamine
(e) 2-(2-pyridylmethylthio)ethylamine
(f) 2-(3-methyl-2-pyridylmethylthio)ethylamine
(g) 2-(3-hydroxy-3-pyridylmethylthio)ethylamine
(h) 2-(2-thiazolylmethylthio)ethylamine
(i) 2-(2-(3-isothiazolylmethylthio)ethylamine
(j) 2-(4-bromo-3-isothiazolylmethylthio)ethylamine
(k) 2-(5-amino-2-(1,3,4)thiadiazolylmethylthio)ethylamine
(l) 3-(2-imidazolylmethylthio)propylamine
(m) 2-(2-oxazolylmethylthio)ethylamine
(n) 2-[(1,2,4)triazolylmethylthio]ethylamine
(o) 2-(3-methoxy-2-pyridylmethylthio)ethylamine
(p) 2-(3-isoxazolylmethylthio)ethylamine
for 2-(5-methyl-4-imidazolylmethylthio)ethylamine in the procedure of Example 1 leads to the production of the following compounds
(a) N-methyl-N'-[2-(5-ethyl-4-imidazolylmethylthio)ethyl]amidinosulphonic acid.
(b) N-methyl-N'-[2-(5-bromo-4-imidazolylmethylthio)ethyl]amidinosulphonic acid.
(c) N-methyl-N'[2-(5-trifluoromethyl-4-imidazolylmethylthio)ethyl]amidinosulphonic acid.
(d) N-methyl-N'-[2-(5-hydroxymethyl-4-imidazolylmethylthio)ethyl]amidinosulphonic acid.
(e) N-methyl-N'-[2-(2-pyridylmethylthio)ethyl]amidinosulphonic acid.
(f) N-methyl-N'-[2-(3-methyl-2-pyridylmethylthio)ethyl]amidinosulphonic acid.
(g) N-methyl-N'-[2-(3-hydroxy-2-pyridylmethylthio)ethyl]amidinosulphonic acid.
(h) N-methyl-N'-[2-(2-thiazolylmethylthio)ethyl]amidinosulphonic acid.
(i) N-methyl-N'-[2(3-isothiazolylmethylthio)ethyl]amidinosulphonic acid.
(j) N-methyl-N'-[4-bromo-3-isothiazolylmethylthio)ethyl]amidinosulphonic acid.
(k) N-methyl-N'-[2-(5-amino-2-(1,3,4)thiadiazolylmethylthio)ethyl]amidinosulphonic acid.
(l) N-methyl-N'-[3-(2-imidazolylmethylthio)propyl]amidinosulphonic acid.
(m) N-methyl-N'-[2-(2-oxazolylmethylthio)ethyl]amidinosulphonic acid.
(n) N-methyl-N'-[2-(1,2,4)triazolylmethylthio)ethyl]amidinosulphonic acid.
(o) N-methyl-N'-[2-(3-methoxy-2-pyridylmethylthio)ethyl]amidinosulphonic acid.
(p) N-methyl-N'-[2-(3-isoxazolylmethylthio)ethyl]amidinosulphonic acid.

EXAMPLE 5

N-Butyl-N'-[2-(5-methyl-4-imidazolylmethylthio)ethyl]amidinosulphonic acid

Substitution of 1-methylthio-1-butylaminomethanesulphonate for 1-methylthio-1-methyliminomethanesulphonate in the procedure of Example 1 will yield N-butyl-N'-[2-(5-methyl-4-imidzolylmethylthio)ethyl]amidinosulphonic acid.

EXAMPLE 6

N-methyl-N'-[2-(5-methyl-4-imidazolylbutyl)]thiourea or N-methyl-N'[2-(5-methyl-imidazolylpentyl)]thiourea when added to a solution of hydrogen peroxide in glacial acetic acid and stirred at ambient temperature will yield N-methyl-N'-[2-(5-methyl-4-imidazolylbutyl)]amidinosulphonic acid and N-methyl-N'-[2-(5-methyl-4-imidazolylpentyl)]amidinosulphonic acid respectively.

EXAMPLE 7

N-[2-(5-methyl-4-imidazolylmethylthio)ethyl]amidinosulphonic acid

Substitution of 1-methylthioiminomethansulphonate for 1-methyliminomethanesulphonate in the procedure of Example 1 will yield N-]2-(5-methyl-4-imidazolylmethylthio)ethyl]amidinosulphonic acid.

EXAMPLE 8

| Ingredients | Amounts |
|---|---|
| N—methyl-N—[2-(5-methyl-4-imidazolylmethylthio)ethyl]amidinosulphonic acid | 150 mg |
| Sucrose | 75 mg |
| Starch | 25 mg |
| Talc | 2 mg |
| Stearic Acid | 2 mg |

The ingredients are screened, mixed and filled into a hard gelatin capsule.

EXAMPLE 9

| Ingredients | Amounts |
|---|---|
| N—methyl-N'—[2-(3-chloropyrid-2-ylmethylthio)ethyl]amidinosulphonic acid | 200 mg |
| Lactose | 100 mg |

The ingredients are screened, mixed and filled into a hard gelatin capsule.

Similarly, the other compounds of Formula 1 may be formulated into pharmaceutical compositions by the procedures of Examples 8 and 9. The pharmaceutical compositions prepared as in the foregoing examples are administered to a subject within the dose ranges given hereabove to block histamine $H_2$-receptors.

What is claimed is:

1. A compound of the formula:

$$\text{Het CH}_2\text{Z(CH}_2)_n\text{NH}-\text{C}\underset{SO_3H}{\overset{NR}{\diagup\!\!\!\diagdown}} \quad \text{I}$$

where Het is a thiazolyl, isothiazolyl, oxazolyl, isoxazolyl, triazolyl or thiadiazolyl group optionally substituted on a ring carbon by a lower alkyl, hydroxy, lower alkoxy, halogen, trifluoromethyl, hydroxymethyl or amino group; Z is sulphur or a methylene group; n is 2 or 3 and R is hydrogen, lower alkyl or Het $CH_2Z(CCH_2)_n$—, Het being attached at a ring carbon, in neutral form or in the form of a pharmaceutically acceptable salt thereof.

2. A pharmaceutical composition having histamine $H_2$-receptor blocking activity comprising in an effective amount to block said receptors a compound of claim 1 in combination with a pharmaceutically acceptable diluent or carrier.

3. A method of blocking histamine $H_2$-receptors which comprises administering to an animal an effective amount to block said receptors of a compound of claim 1.

* * * * *

UNITED STATES PATENT AND TRADEMARK OFFICE
CERTIFICATE OF CORRECTION

PATENT NO. : 4,375,472

DATED : March 1, 1983

INVENTOR(S) : Graham J. Durant, Rodney C. Young and Zev Tashma

It is certified that error appears in the above—identified patent and that said Letters Patent is hereby corrected as shown below:

Column 2, line 23, "were" should read -- where -- .

Column 6, line 56, $CH_2Z(CCH_2)_n-$ should read -- $CH_2Z(CH_2)_n-$ -- .

[SEAL]

Signed and Sealed this

Third Day of May 1983

Attest:

Attesting Officer

GERALD J. MOSSINGHOFF

Commissioner of Patents and Trademarks